United States Patent
Heynen et al.

(10) Patent No.: US 10,268,647 B2
(45) Date of Patent: Apr. 23, 2019

(54) ASSET CATALOG LAYERED IMAGE SUPPORT

(71) Applicant: Apple Inc., Cupertino, CA (US)

(72) Inventors: Patrick O. Heynen, Redwood City, CA (US); Jonathan J. Hess, Los Altos, CA (US); Blake R. Seely, San Francisco, CA (US); James T. Turner, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 14/871,849

(22) Filed: Sep. 30, 2015

(65) Prior Publication Data

US 2016/0358356 A1    Dec. 8, 2016

Related U.S. Application Data

(60) Provisional application No. 62/171,959, filed on Jun. 5, 2015.

(51) Int. Cl.

| | |
|---|---|
| *G06F 3/14* | (2006.01) |
| *G06T 5/50* | (2006.01) |
| *G06T 7/00* | (2017.01) |
| *G09G 3/00* | (2006.01) |
| *G09G 5/00* | (2006.01) |

(Continued)

(52) U.S. Cl.
CPC ............ *G06F 16/51* (2019.01); *A61F 13/00* (2013.01); *G06F 3/14* (2013.01); *G09G 5/377* (2013.01); *G06F 3/04845* (2013.01); *G06F 17/214* (2013.01); *G06F 17/2288* (2013.01); *G06T 5/50* (2013.01); *G06T 7/97* (2017.01); *G06T 11/60* (2013.01); *G06T 2207/20221* (2013.01);

(Continued)

(58) Field of Classification Search
None
See application file for complete search history.

(56) References Cited

U.S. PATENT DOCUMENTS

| | | | |
|---|---|---|---|
| 8,468,498 B2 | 6/2013 | Lee et al. | |
| 2002/0184610 A1* | 12/2002 | Chong | G06F 8/20 717/109 |

(Continued)

*Primary Examiner* — YuJang Tswei
(74) *Attorney, Agent, or Firm* — Womble Bond Dickinson (US) LLP

(57) ABSTRACT

Systems and methods are disclosed for authoring, deploying, and executing layer stack images for applications directed to a plurality of target devices. Resources to implement the layer stack images are compiled into an asset catalog database for each image in each layer stack image for each target device. Derivative resource products, such as a flattened version of the layer stack images and a "blurred" version of layer stack images can be generated and stored in the asset catalog at compile and build time. Three-dimensional effects implemented using the layer stack images can be implemented using an application programming interface that accepts legacy two dimensional images can be used to receive the layer stack images. An platform framework implements logic that detects the type of image requested via the API is a layer stack image or a conventional flat image. Third party layer stack images can be received and displayed at run-time or compile time. Images that make up a layer stack image can be locally-stored, externally referenced, or both. A layer stack image can, itself, refer to other layer stack images.

30 Claims, 12 Drawing Sheets

(51) Int. Cl.
*A61F 13/00* (2006.01)
*G06F 16/51* (2019.01)
*G06F 17/21* (2006.01)
*G06F 17/22* (2006.01)
*G06T 11/60* (2006.01)
*G09G 5/377* (2006.01)
*G06F 3/0484* (2013.01)

(52) U.S. Cl.
CPC ............ *G09G 3/003* (2013.01); *G09G 5/005* (2013.01); *G09G 2370/022* (2013.01)

(56) References Cited

U.S. PATENT DOCUMENTS

| | | | | |
|---|---|---|---|---|
| 2005/0001853 | A1* | 1/2005 | O'Donnell | G06T 15/503 345/634 |
| 2007/0070066 | A1* | 3/2007 | Bakhash | G06F 3/04815 345/419 |
| 2012/0331108 | A1* | 12/2012 | Ferdowsi | H04L 67/06 709/219 |
| 2013/0236119 | A1* | 9/2013 | Campbell | G06T 11/60 382/284 |
| 2014/0047413 | A1* | 2/2014 | Sheive | H04L 65/403 717/110 |
| 2014/0109046 | A1* | 4/2014 | Hirsch | G06F 9/44 717/120 |
| 2015/0301721 | A1* | 10/2015 | Clark | H04L 67/10 715/780 |

* cited by examiner

400

| | | |
|---|---|---|
| 405→ | Layer Stack Image name: | "Race to the Finish" Game Logo |
| 406→ | Layer Stack Filename | local://resources/LS/GameLogo |
| 410→ | Layer 1 | |
| 411→ | Image filename | http://GameCo/image/Logo1.png |
| 412→ | Z-depth | 1 |
| 413→ | XY position | 0, 0 |
| 414→ | Size | 360x180 pixels |
| 415→ | Opacity | 15% |
| 416→ | Text | "Race to the Finish" |
| 417→ | Font | Calibri |
| 418→ | Font Size | 18 pt |
| 419→ | Layer effect | Drop Shadow -2px |
| 430→ | Layer 2 | |
| 431→ | Image filename | local://resources/images/Car1.png |
| 432→ | Z-depth | 2 |
| 433→ | XY position | 120,10 |
| 434→ | Size | 120x60 pixels |
| 435→ | Opacity | 55% |
| 436→ | Text | "Herbie" |
| 437→ | Font | Calibri |
| 438→ | Font Size | 15 pt |
| 439→ | Layer effect | null |
| 450→ | Layer 3 | |
| 451→ | Image filename | local://resources/images/Track3.png |
| 452→ | Z-depth | 3 |
| 451→ | XY position | 120,0 |
| 454→ | Size | 240x120 pixels |
| 455→ | Opacity | 85% |
| 456→ | Text | "Par for the Course" |
| 457→ | Font | Calibri |
| 458→ | Font Size | 15 pt |
| 459→ | Layer effect | null |

*FIG. 4*

ASSET CATALOG LAYERED IMAGE SUPPORT

RELATED APPLICATIONS

This application claims priority under 35 U.S.C. § 119(e) of U.S. Patent Application No. 62/171,959, filed Jun. 5, 2015, and entitled "ASSET CATALOG LAYERED IMAGE SUPPORT," which is incorporated herein by reference to the extent that it is consistent with this disclosure.

TECHNICAL FIELD

This disclosure relates to the field of software development, deployment, and run-time features of visual aspects of a user interface.

BACKGROUND

A user interface control, such as a button, a tool bar icon, or a dialog box can have an image associated with the control. A user interface developer kit can contain code to display a two-dimensional ("2D") version on the control. Some modern user interface applications have a three-dimensional ("3D") feature for an image on a control. The 3D image can have an animation effect giving the image the appearance of a slight jiggling motion. The 3D image can be made up of several separate images, each having properties. Implementation of 3D image effects can require a substantial amount of software coding and image bookkeeping. Bookkeeping can include obtaining a correct resolution and size of each of the several separate images in a 3D image, the z-depth, position information, opacity, and other information of each image in the 3D image. A manufacturer of electronic devices that support 3D image effects may manufacture devices having different display screen sizes and resolutions. Each device may need to implement the 3D image a little differently based upon display and device characteristics. In addition, software developed using 3D images for a device may not be backward-compatible with older devices that can display 2D images but may not be able to implement the 3D images or animation effects.

Currently, each third party software developer that writes a software application for an electronic device of a manufacturer would need to develop her own 3D image support for each device that the manufacturer produces.

SUMMARY OF THE DESCRIPTION

Embodiments are described for authoring, compiling, building, and deploying applications that use layer stack images. The applications can be developed for a plurality of target electronic devices. Layer stack images can display 3D images and animated effects for the layer stack images. A single layer stack image ("singleton") can be developed by a third party, such as a content provider. The singleton layer stack image can be received and displayed by the application. Layer stack images can contain an external reference to one or more layer images that are stored remotely from the application. At compile time, the externally referenced image can be retrieved and incorporated into the application. At run-time, the application can determine whether the externally referenced image has changed. If so, the application can obtain the updated image and incorporate the updated image into the application. The application can use an application framework that is backward compatible with existing 2D image development. The developer can use the same application programming interface (API) that is used for a 2D image to call for rendering of a 3D layer stack image. The developer can continue to use the same API for 2D images without having to modify legacy software. The application framework can detect that a 3D image is being referenced in an API call, and the application framework can render and display the 3D effects of the layer stack image. If a particular target device cannot support 3D images, the application can present a flattened image in lieu of the 3D image. The flattened image, and other derivative products of the layer stack image, can be computed at compile time rather than at run-time. A plurality of layer stack images that use a common image, such as in a leaderboard entry for a game, can each have a reference to a single copy of the image they have in common, thereby saving space.

In a first embodiment, a work flow method for authoring resources and developing and deploying an application using the resources can include generating resources for the application, including at least one layer stack image. In an embodiment, the application can utilize upon an application framework and an application programming interface (API) for deploying 3D images that uses the same API as for conventional two dimensional images. A developer can write code that supports a plurality of target devices, then compile and build the application, generating run-time code and resources for the plurality of target devices. In an embodiment, the compile and build process can generate a universal application that can be run on a plurality of targets without specifying particular targets. In an embodiment, a thinning process can remove resources or components that are not needed for a particular target. In an embodiment, when targeting older devices that do not support 3D rendering and effects, thinning can eliminate the individual layers, media, and other extraneous components and just leave the flattened image that will be displayed in lieu of the layer stack image. In some embodiments, the developer can upload the application to an application store or equivalent site where users can download the application to one or more target devices. In an embodiment, a user can download the application to a particular target device, and the process of downloading the application to the particular target device downloads only the resources necessary to run the application on the particular target device. In another embodiment, when the user download's the application to a particular target device, the application still contains at least some resources for a target device other than the particular target device of the user.

In another embodiment, an author of layer stack image resources can define a new layer stack image. In an embodiment, a layer stack image can be generated for a universal application that can be run on a plurality of target devices without specifying particular target devices. In an embodiment, the author can select one or more target devices for the layer stack image. A target device can include target device types such as a desktop computer, a laptop computer, a smart phone, a tablet computer, or a media presentation device such as Apple TV®. Target devices can include one or more manufacturers of one or more models of a same type of target device. Target devices can include one or more manufacturers of one or more types of target device and one or more models of a type of target device. An author can specify an image for a layer stack. In an embodiment, the author can modify and store a version of an image for a particular target device. Alternatively, or in addition, the author can specify an image that can be used by multiple target devices without alteration. In embodiment, two different layer stack images can reference a same image for a layer of each respective layer stack image. An author can specify one or parameters and parameter values for a layer, such as image filename, image type, image size, image resolution, text associated with the image, an font characteristics for the text. In an embodiment, the image can be stored remotely on a third party server. The above operations can be repeated for additional layers of the layer stack image. Then the image layers and associated parameters and parameter values can be stored.

In another embodiment, a layer stack image can be compiled and stored in an assets catalog database that can be accessed by an application at run-time. The assets catalog database can contain source artifacts for a layer stack image, such as the images, video, animations, audio, or text that make up the layers in the layer stack images, and metadata that represents parameters and parameter values associated with a layer stack image and the layers that make up the layer stack image. The compile process can generate derived products for a layer stack image such as a flattened (2D) image of the 3D layer stack image and a blurred image that is used in conjunction with 3D animated effects of a layer stack image. The layer stack images, metadata, and derived products can all be stored in an asset catalog database that is accessible to the application at run-time.

In yet another embodiment, an application that uses layer stack images can be launched on a target device. In an embodiment, the application can receive a layer stack image from a third party and display the layer stack image on the target device. In an embodiment, a layer stack image can include one or more layers that reference an image that is stored remotely ("externally referenced image"), such as on a third party server. At run-time, the application can determine whether an updated version of the externally referenced image exists at the third party server. If so, the application can retrieve the updated externally referenced image, generate any derived products such as a flattened image and a blurred image of corresponding to the layer stack image, and generate one or more 3D effects for the layer stack image. In an embodiment, the application can detect a manufacturer, a type, and a model of the target device, and whether the target device can support the one more 3D effects of a layer stack image. If not, the application can display the flattened image corresponding to the layer stack image in lieu of the layer stack image.

Some embodiments described herein can include one or more application programming interfaces (APIs) in an environment with calling program code interacting with other program code being called through the one or more interfaces. Various function calls, messages or other types of invocations, which further may include various kinds of parameters, can be transferred via the APIs between the calling program and the code being called. In addition, an API may provide the calling program code the ability to use data types or classes defined in the API and implemented in the called program code.

At least certain embodiments include an environment with a calling software component interacting with a called software component through an API. A method for operating through an API in this environment can include transferring one or more function calls, messages, other types of invocations or parameters via the API.

Other features and advantages will be apparent from the accompanying drawings and from the detailed description.

BRIEF DESCRIPTION OF THE DRAWINGS

Embodiments of the invention are illustrated by way of example, and not by way of limitation, in the figures of the accompanying drawings in which like reference numerals refer to similar elements.

FIG. 4 illustrates a data structure for specifying parameters and parameter values of an example layer stack image.

DETAILED DESCRIPTION

In the following detailed description of embodiments, reference is made to the accompanying drawings in which like references indicate similar elements, and in which is shown by way of illustration manners in which specific embodiments may be practiced. These embodiments are described in sufficient detail to enable those skilled in the art to practice the invention, and it is to be understood that other embodiments may be utilized and that logical, mechanical, electrical, functional and other changes may be made without departing from the scope of the present disclosure. The following detailed description is, therefore, not to be taken in a limiting sense, and the scope of the present invention is defined only by the appended claims.

Embodiments are described for a first process to request that a second process, or any subsequent process in a sequence of processes (termed, "remote process") to perform work on behalf of the first process and for the remote process to securely provide a guaranteed response to the first process, without passing the response through any intervening processes in the sequence.

Figure 1:
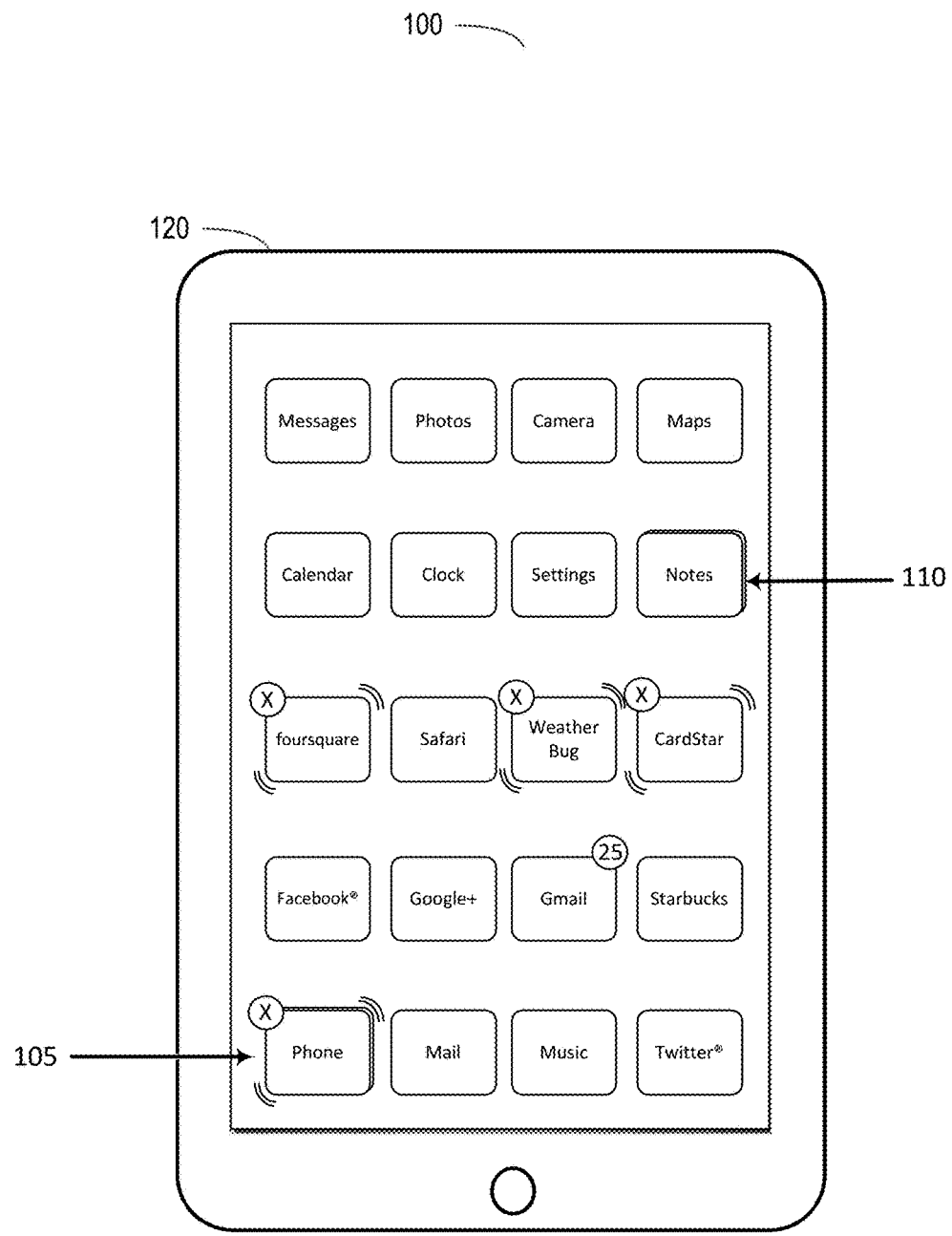
FIG. 1 illustrates a screen shot of a smart phone having icons each composed of a layer stack image, according to some embodiments.

FIG. 1 illustrates a screen shot 100 of a smart phone 120 having icons composed of layer stack images, according to some embodiments.

Icons, such as Notes icon 110 and Phone icon 105, can be generated for a smart phone using layer stack images in an application such as a home screen application. A layer stack image, as the name implies, is an image that can include multiple layers to generate the image. A layer stack image can have a three-dimensional ("3D") appearance. A layer stack can have one or more behaviors, such as a "jittering" visual appearance, a blurring appearance in conjunction with a motion or animation, or an audio sound related to a visual behavior. A blurred image can be generated from the images that make up the layer stack image to implement the blurred appearance. A layer stack image can also have a flattened appearance, as a two-dimensional ("2D") appearance. A 2D appearance can be presented on an electronic device that does not support 3D layer stack images. A 2D appearance can also be temporarily displayed in place of the layer stack image during a time when an electronic device is computing a 3D effect for the layer stack image. In an embodiment, the flattened image and blurred image (collectively, "derived products") for a layer stack image in an application can be generated at a compile and build time of the application, rather than at run-time of the application.

Layers in a layer stack image can include one or more graphical layers and one or more textual layers. Each layer can have its own properties, as described below with reference to FIG. 4.

Figure 2:
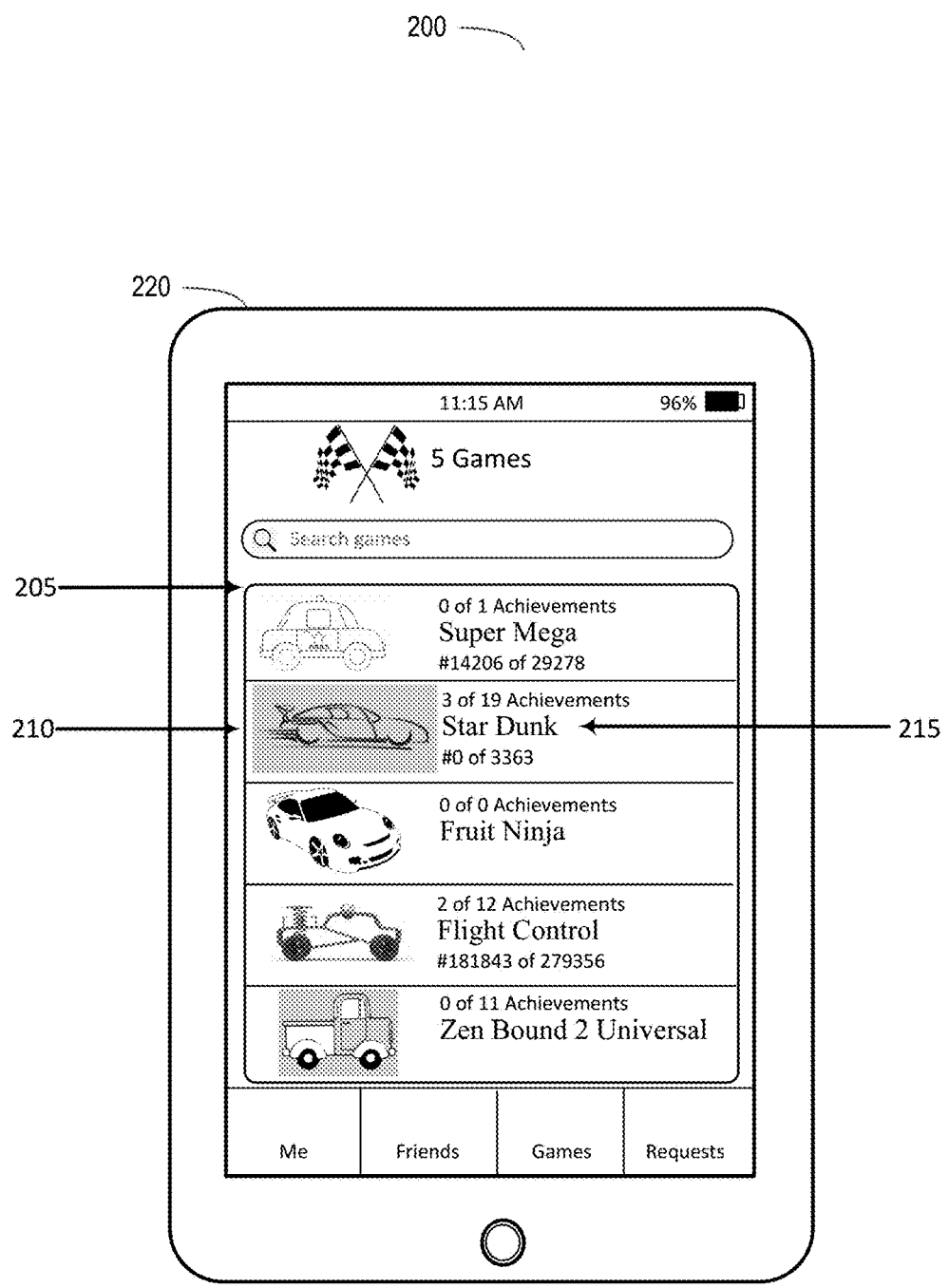
FIG. 2 illustrates a screen shot of a smart phone having a game leaderboard composed of layer stack images, according to some embodiments.

FIG. 2 illustrates a screen shot 200 of a smart phone 220 having a game leaderboard 205 composed of layer stack images, according to some embodiments.

Leaderboard 205 of a game can have a layer stack image for each player listed in the leaderboard 205. Each layer stack image can have one or more graphical layers to generate, e.g., player icon 210. A layer stack image can further include a textual layer for a name (e.g., "StarDunk"), another textual layer for the player's performance (e.g., "3 of 19 achievements"), and a player standing (e.g., "#0 of 3363"). A plurality of leaderboard entries can each contain a reference to a single copy of an image that provides a common background for the plurality of leaderboard entries. Information for each layer can be obtained by a reference to a source of the information. For example, player icon 210 and player name, performance, and standing information 215 could be obtained by reference to a multi-game player site such as Apple® Game Center. When a leaderboard application launches, the referenced information can be obtained and the 3D images for each layer stack image can be generated.

In an embodiment, each layer image stack for a player can be generated by the remote referenced location, such as Apple® Game Center, and the leaderboard application can obtain the generated 3D image stack from the remote referenced location. For example, for a given game, a game application can specify a layer stack image for each of the first five players in a game by reference to a remote location. The remote location could receive a request from the application to generate a layer stack image each of the first five players of the game. The application could receive the five layer stack images from the remote location and present the five layer stack in a leaderboard that is, itself, a layer stack image that references five externally referenced layer stack images (one for each of the first five players).

Thus, a layer stack image can contain one or more layer stack images by reference. Additionally, one or more layer stack images, or individual layers within a layer stack image, can be obtained at run-time from a location referenced within a layer stack image.

Figure 3:
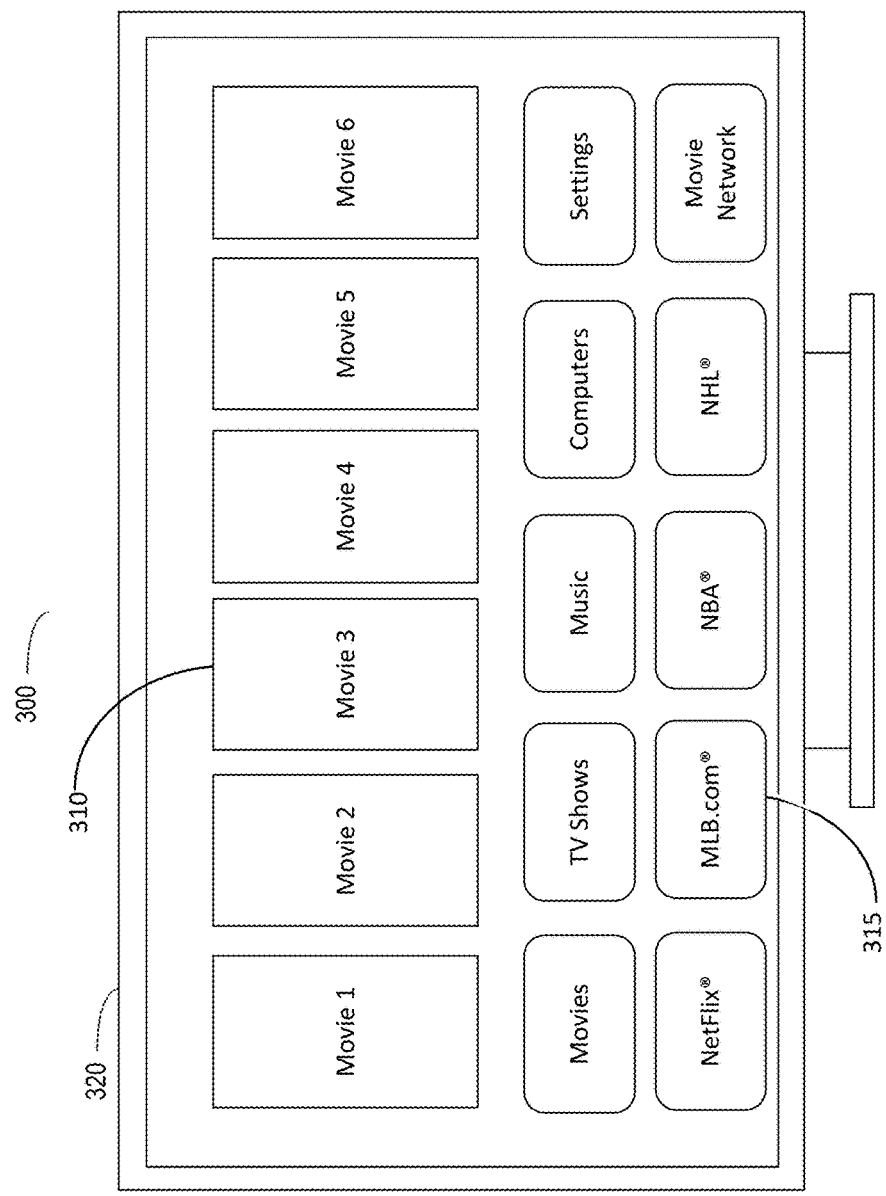
FIG. 3 illustrates a screen shot of a media presentation device composed of a plurality of layer stack images, according to some embodiments.

FIG. 3 illustrates a screen shot 300 of a media presentation device 320, e.g. Apple TV®, composed of a plurality of layer stack images, according to some embodiments.

A screen shot 300 shows poster art 310 for a plurality of movies and an icon 315 for a plurality of features, links, or functions of the presentation device 320.

Poster art 310 can be generated using layer stack images. In an embodiment, an application on presentation device 320 can contain request a plurality of poster art 310 layer stack images from one or more third party content providers. Example poster art 310 can include one or more graphical image layers, one or more textual layers, and can include video clip, an animation, or an audio clip associated with the layer stack image. Poster art layer stack image 310 can have a 3D visual appearance and can have one or more animation or motion effects generated from the layers in the layer stack. In an embodiment, the application on the presentation device 320 can optionally generate a flattened 2D image for use on the presentation device 320. In an embodiment, the third party content provider can provide the flattened image of the layer stack image.

Screen shot 300 also indicates a plurality of icons 315 for features, links, or functions on the presentation device 320. For example, icon 315 can launch functionality associated with the icon "MLB.com®." Icon 315 can include one or more graphical image layers, one or more textual layers, and can include video clip, an animation, or an audio clip associated with the layer stack image 315. For example, a first layer of the icon 315 may be a graphical image of the logo for Major League Baseball ("MLB®"). MLB® may, on occasion, change their logo. The layer stack image 315 can reference the MLB® logo at a website controlled by MLB®. On launch of the application, or on request for display of the layer stack image 315, the application can check the MLB® website to see if there is an updated logo graphic. If so, the application can download the updated logo image and incorporate the updated logo image into the layer stack image for icon 315.

Poster art 310 and/or icons 315 can have an animated motion produced by the layer stack images on presentation device 320. The animated motion can indicate which poster art 310 or icon 315 has the focus of the application, in response to an input device. A presentation device 320 may have a remote control (not shown). Operation of the remote control can select a current poster art 310 or icon 315. A poster art of 310 or icon 315 that has the focus of the application can also play an audio clip referenced in the layer stack image. In an embodiment, the application can detect a language selection on the presentation device. In response to detecting a particular language selection, the layer stack image can retrieve a textual translation of a poster art 310 or icon 315 and/or video clip, an audio clip, or an audio/video clip in the selected language. The layer stack image can then present the layer stack image in the selected language.

FIG. 4 illustrates a data structure 400 for storing parameters and parameter values of an example layer stack image. A layer stack image can be generated within an Integrated Development Environment ("IDE") or within a resource editor. Resources (also termed, "source artifacts") for composing the layer stack image can be located on a local storage of a computing device of an application developer or content author. In an embodiment, one or more of the source artifacts can be located in a remote location, such as a network drive or third party content provider. In an embodiment, a third party content provider can be a developer site, such as Apple® Developer, that may contain a library of source artifacts from which a developer may select and download, or reference within a layer stack image. In an embodiment, a third party content provider can be a party that owns, or is licensed to provide, content for one or more layers of a layer stack image. For example, a third party may be licensed to provide poster art for movies that the third party is licensed to distributed. In another example, a third party, such as a streaming service, may be licensed to display a logo owned by another party. For example, a streaming service such as NetFlix® (third party) may be licensed to display a logo for Columbia Broadcasting System (CBS) in connection with NetFlix® streaming content produced and owned by CBS. NetFlix® can provide a layer stack image with a layer containing the CBS "eye" logo to an application on a presentation device 320 that will stream the content. The application can receive the layer stack image, generated by NetFlix®, with the reference to the CBS logo contained therein. Thus, layer stack images enable authors to generate a single layer stack image that contains content provided by one or more third parties and to display the layer stack image on a presentation device 320 using special effects, like motion or audio, without the author having to write code to implement the layer stack image functionality.

A layer stack image data structure 400 can include a textual, human-readable, name for the layer stack image 405. A layer stack image can also include a filename 406 for storing the layer stack image data structure 400. In addition, a layer stack image can include a plurality of layers 410, 430, and 450.

A layer, e.g. layer 1 410, can include an filename for an image 411 for the layer, a Z-depth 412 for the layer within the layer stack image, an XY position 413 for a location for this layer within the layer stack image, a size 414 of the image, a opacity of the image 415, text 416 that may be associated with the layer, and a font 417 and font size 418 of the text 416 (if any) that may be associated with the layer. In addition, a layer can have a reference to layer effect 419. A layer effect 419 can be a video layer, a simple animation, a vector shape with metadata for color, stroke width, affine transform, gradients with a clipping path, or a drop shadow. In an embodiment, a layer effect 419 can comprise an audio clip.

In FIG. 4, layer stack image data structure 400 is populated with example data to illustrate features of a layer stack image. The example data is intended to be illustrative and not limiting. The example data is directed toward an entry in a leaderboard of a car racing game, "Race to the Finish."

Example layer 1 (410) is for a logo for the game. The image filename 411 indicates that the logo is located at a remote website operated by "GameCo." GameCo is free to change their logo at any time. When the layer stack image is loaded by a leaderboard application at run-time, the application can reference the logo image at GameCo's website and incorporate the logo into the layer stack image. In an embodiment, when an image is externally referenced, a current copy of the image can be downloaded from the external location and the image can be stored locally. In addition, metadata can be downloaded indicating how current the image is, such as a date/time of last modification of the externally referenced image, file size of the externally referenced image, or other identifying metadata. The metadata can be stored locally and used later to determine whether the externally referenced image has changed since it was last referenced. The logo may also have text associated with it, e.g. "Race to the Finish," and the text can be displayed in, e.g. Calibri, 18 point font. The layer stack image can also contain video layer, an animation, or an audio clip, such as a car rev'ing its motor, that is referenced at GameCo's website. If the layer stack image was for displaying a particular game player's data on the leaderboard, each player may have a different car image and different audio clip for the player's car sound.

Example layer 2 (430) is for a player's car for the game. The image filename 431 indicates that the car image is located at the remote website operated by "GameCo." When the layer stack image is compiled, the compiler can retrieve the car image stored at GameCo, generated the layer stack image using the car image, and generated derived products such as a blurred image and a flattened image of the layer stack image, using the retrieved car image. GameCo is free to change the car image for a game at any time. When the layer stack image is loaded by the leaderboard application at run-time, the application can retrieve the car image at GameCo's website, determine whether the image has changed from the time that the layer stack image was compiled, incorporate the car image into the layer stack image, and generate the derived products based upon the newly retrieved image.

Example layer 3 450 is directed to an image of a race track. As indicated in image filename 451, the race track can be a locally stored image. Example layer 3 450 can have text 456 associated with the layer, e.g. "Par for the Course," that is displayed on layer 3 450 using font 457 and font size 458, e.g. Calibri 15 point, respectively.

These are example parameters and parameter values of a layer of an layer stack image. A layer can have more, or fewer, parameters. When the layer stack image is compiled by resource compiler or other compiler, metadata for the layer stack image and associated layers for storing in an asset catalog database. An application using the asset catalog database can request, and retrieve, metadata and resources from the asset catalog database for use by the application. Additionally, the application, or an application framework, can use the metadata to retrieve and process additional resources using the references in the parameters. Then the resource, e.g. an image layer stack, can be presented to a user of the application.

Figure 5:
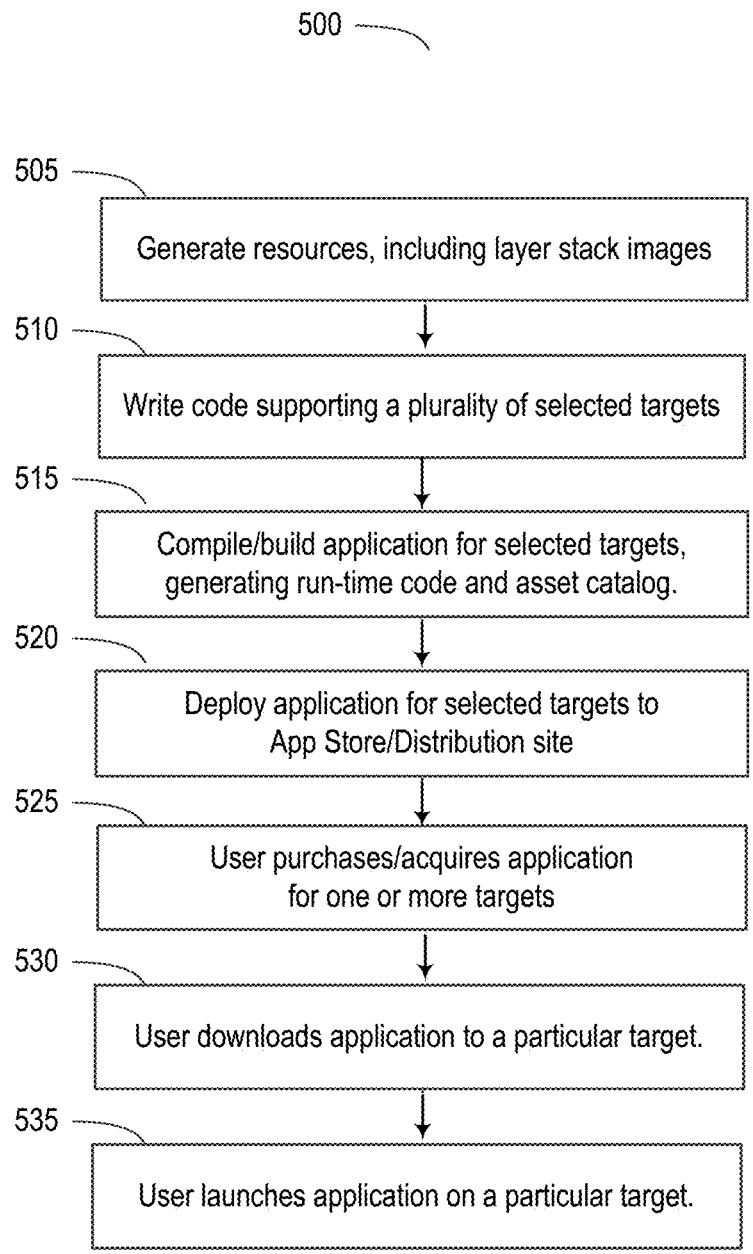
FIG. 5 illustrates, in block diagram form, a method of a work flow for authoring, developing and deploying an application that supports multiple target devices that use layer stack images, according to some embodiments.

FIG. 5 illustrates, in block diagram form, a method 500 of a work flow for developing and deploying an application that supports multiple target devices that use layer stack images, according to some embodiments.

In operation 505, an author or developer (collectively and individually, "developer") can generate resources for an application, including layer stack images, as described above.

In operation 510, a developer can write code for an application that uses the resources generated in operation 505. The application can be directed to multiple types of target devices, such as a desktop computer, a tablet computer, or a smart phone. In an embodiment, the application can be directed to a plurality of models of one or more of these target device types. In an embodiment, the developer can preselect the targets for each resource generated for the application. In another embodiment, the developer can generate a universal application package without having to specify any particular target devices or device types.

Components in a universal application package may include executables (or intermediate code) and/or assets to allow an associated application to be installed into multiple types of target devices. Assets may be stored in an asset catalog. The assets can be application data accessed during runtime of the application, such as image files, shaders, textures, or other applicable data resources, etc. Each asset may be developed/designed to target certain device capabilities or device traits, for example, represented via a key associated with the asset. The intermediate code can be, for example, an intermediate representation of code that is create (e.g. compiled) from a source code but is not executable, and a further compilation can create a plurality of executable applications for a corresponding plurality of different devices.

An application thinning mechanism can select (or pick) a subset of components from a universal application to assemble an application variant to be distributed and installed to a specific type of device(s). The universal application may include every component, such as asset, resource or executable, built/developed for targeted device attributes to allow installing the application to multiple types of devices based on one common application package.

The thinning mechanism can reduce the size of or thin down (e.g. by removing certain application components) the universal application for a target type of devices. For example, the thinning mechanism (e.g. tool) can use a trait vector (e.g. a set of device attributes) associated with a type of devices to iterate through the components (e.g. an asset catalog in the application package) and identify assets to be included or packaged into in each target device specific application or application variant (while excluding other assets that are designed for use on other devices). Universal application development is described in the Applicant's related U.S. patent application Ser. No. 14/732,610, entitled "CAPABILITY ATTRIBUTES BASED APPLICATION PACKAGING," filed Jun. 5, 2015, and is incorporated by reference here in its entirety.

In operation 515, a compile and build of the application can be generated. In an embodiment, compile of the resources can be a separate operation from compile and build of the application. In an embodiment, an integrated development environment can compile the resources and code in a single operation. In an embodiment, the compile and build operation can include a linking operation that links compiled code with other referenced compiled code. In an embodiment, linking with other object code can occur at run-time. The compile and build operation can generate executable application code and a database of compiled resources, including one or more layer stack images. In an embodiment, the compiled database of resources comprises an asset catalog database. The compiled resources can include metadata for individual resources within the compiled database of resources. The compiled resources can include resources and metadata for the multiple target devices. In an embodiment, compiled resources, such as layer stack images, that reference a same resource, such as an image, can include a single copy of the same resource and each resource that utilizes the same resource can contain a reference to the single copy of the same resource. The compiled resources can be stored in a compiled resources (or "assets catalog") database.

In operation 520, the application, including the compiled resources database, can be deployed to a distribution point, such as an online application store. Once deployed, the application can be downloaded by one or more users to one or more user target devices.

In operation 530, a user can acquires rights to use the application on one or more target devices. In an embodiment, a user can log on to a user authentication account. In an embodiment, a user can have a plurality devices registered with the user authentication account. When the user acquires rights to use the application, the user can acquire rights to use the application for one or more of the user's target devices. In an embodiment, the user can acquire rights to use the application for all of her target devices that are supported by the application. In an embodiment, the user can acquire rights to use the application on any target device that is supported by the application.

The user can download the application to a target device of the user. In an embodiment, the process of downloading the application to a target device of the user can involve downloading a thinned version of a universal application that is specific to the target device of the user by virtue of the thinning. The download process can extract only the resources that are specific to the target device installation on the target device. In an embodiment, the download process can download the application to the target device with the resources for all of the target devices, and at run-time, only those resources that are specific to the target device are retrieved and instantiated.

In an embodiment, the download process can check for updates to resources referenced within a layer stack image, such as updated images, audio or text that are externally referenced in one or more layer stack images. If a resource is updated at download time, the derivative products, such as a flattened image of a layer stack image and a blurred image of a layer stack image, can be regenerated before download. In addition, referenced audio and/or video can be converted to an appropriate data type (e.g. MP3 or MP4) or to a different resolution (e.g. lower resolution) to save space, depending upon a particular target device type. In an embodiment, the regenerated and stored derivative products can be stored at the deployment site and downloaded to the target device.

In operation 535, a user can launch the application on a particular target device. When the user launches the application, the application can retrieve one or more resources that are specific to the application and compute one or more 3D effects associated with the resource. In an embodiment, if the target device does not support the 3D effect of a layer stack image, the application, or an application framework used by the application, can alternatively display a flattened image of the layer stack image. In such an embodiment, the application can forego generating the 3D effect of the image, as it will not be used. In an embodiment, the flattened image of a layer stack can be displayed while the 3D effect for the layer stack is being generated.

Figure 6:
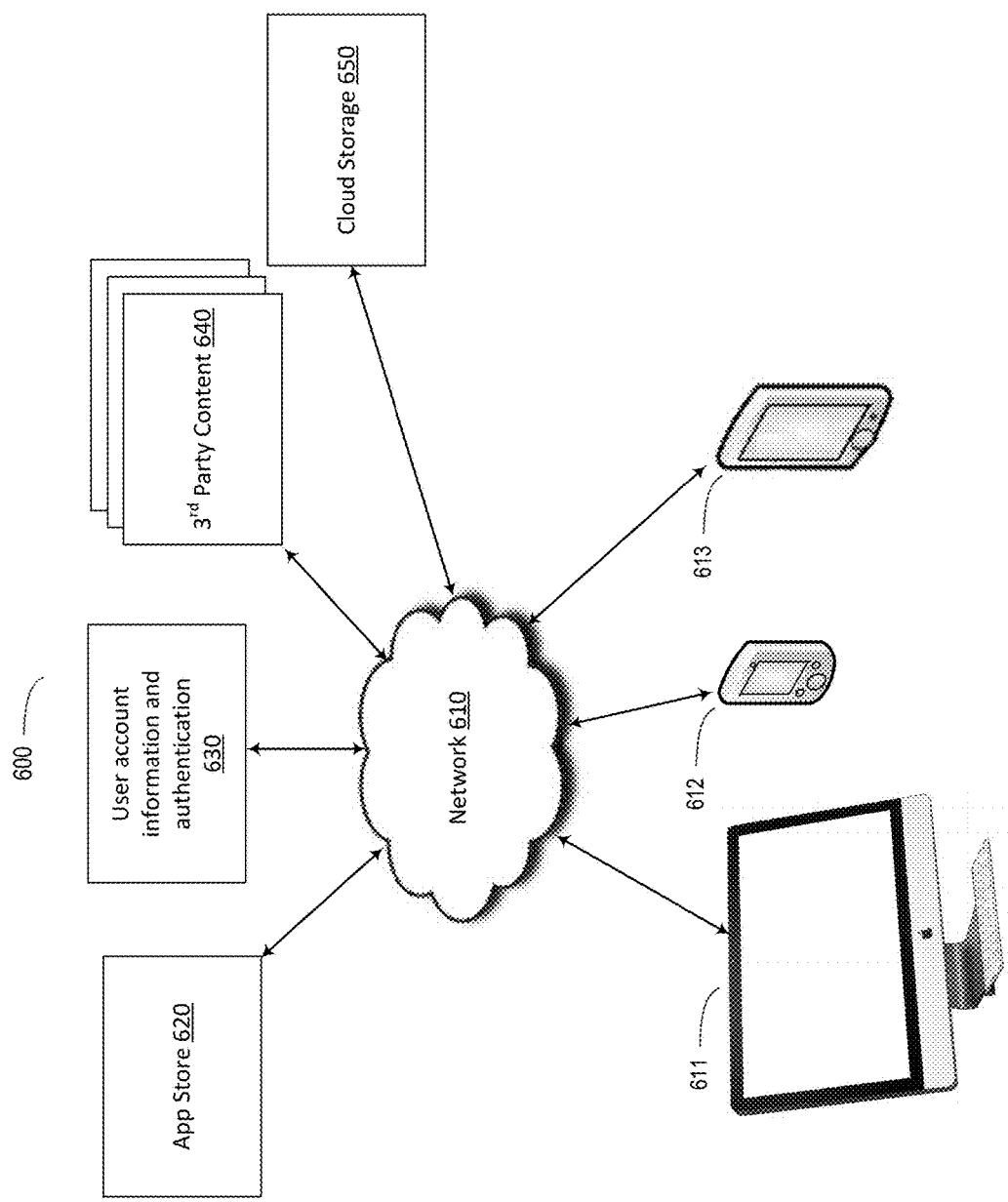
FIG. 6 illustrates, in block diagram form, a system for deploying, distributing, and using an application that supports multiple target devices that use layer stack images, according to some embodiments.

FIG. 6 illustrates, in block diagram form, a system 600 for deploying, distributing, and using an application that supports multiple target devices that use layer stack images, according to some embodiments.

A system 600 can include one or more user target devices, such as desktop computer 611, smart phone 612, or a tablet computer 613. A user can have a user account 630 that is accessed across network 610. At the user account 630, the user's devices 611-613 can be registered with the user. An application can be deployed at an Application Store (also termed, "App Store") 620. As described above, with referenced to FIG. 5, users can acquire rights to download and use an application through App. Store 620. In an embodiment, the downloaded application can be stored in cloud storage 650 associated with a user and/or user account 630. From cloud storage 650, a user may download the application to one or more of her target devices 611-613

When a user launches the application, the application can check for updated layer stack images resources from one or more third party content server 640. In addition, an application may retrieve one or more layer stack images from third party content server 640. For example, if the application implements a presentation device 320, as in FIG. 3 above, one or more of poster art 310 and icons 315 may be retrieved from third party content server 640, rather than being stored in the application's asset catalog database of application resources. The asset catalog database for the application may, instead, store a placeholding layer stack image for a plurality of display screen positions and retrieve a complete layer stack image for each placeholder layer stack image from the third party content server 640 and render the layer stack images in the locations specified by the placeholder layer stack images.

Figure 7:
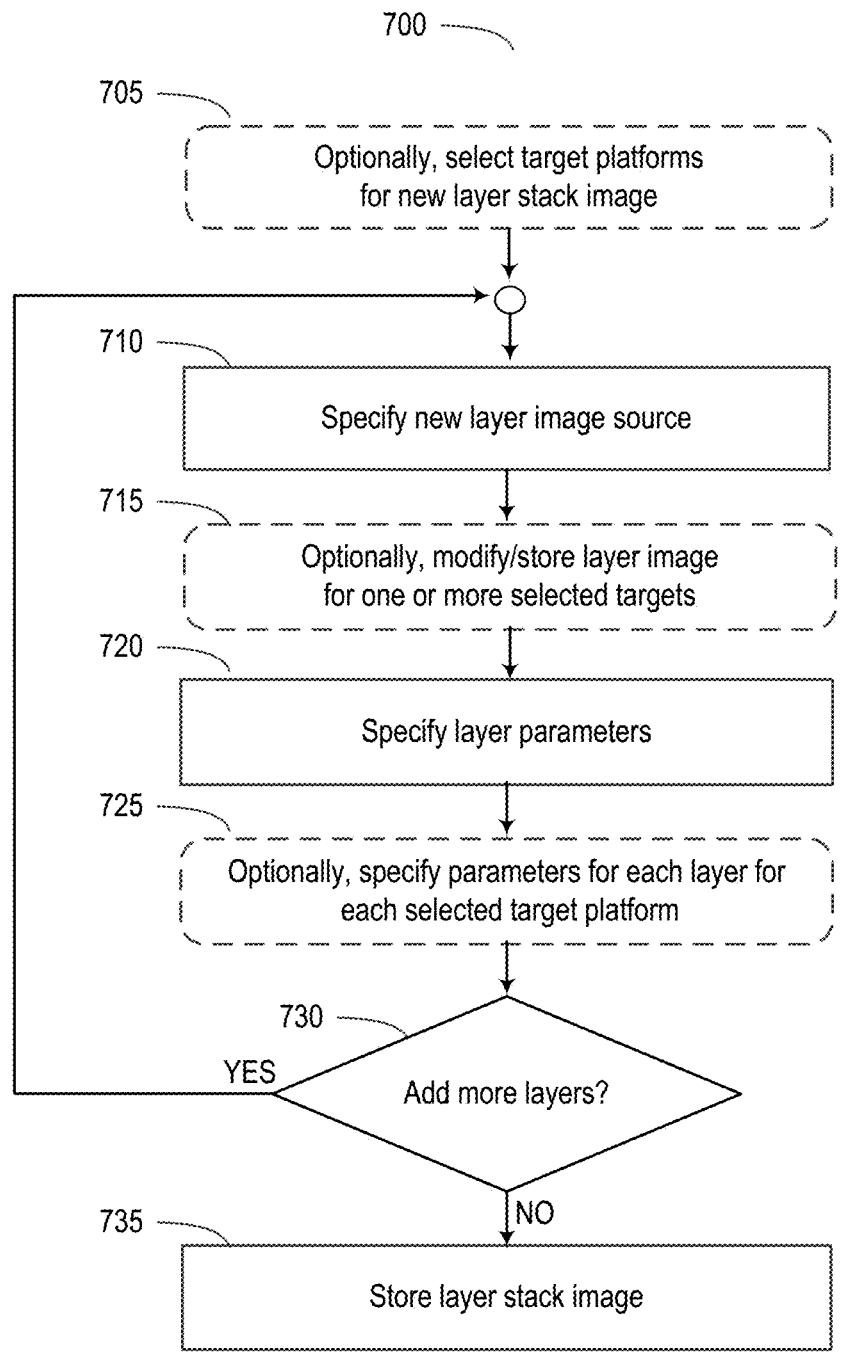
FIG. 7 illustrates, in block diagram form, a method of defining a new layer stack image.

FIG. 7 illustrates, in block diagram form, a method 700 of defining a new layer stack image. The method can be practiced from within a resource editor or an integrated development environment that includes a resource editor.

In operation 705, an author or developer (collectively and individually, "developer") can optionally specify target device platforms for the new layer stack image. In an embodiment, a developer can specify a set of one or more target devices for all resources being added to an application. In another embodiment, a developer can develop a universal application that can be run on a wide variety of target devices without preselecting any particular device targets for the application. A target device may include a desktop computer, a laptop computer, a smart phone, a tablet computer, or other display device. A target device can further include more than one manufacturer or model of target device of each of the target device types (e.g. multiple smart phones by one or more manufacturers).

In operation 710, the developer can specify a layer image source for a new layer of a layer stack image. The layer image source can be a local drive, a cloud storage, e.g. a developer site having resources for use in authoring an application development, or a remote location of a third party, such as a content provider, game host, or other provider of content.

In operation 715, the developer can optionally modify and/or store a layer image for one or more targets. For example, a developer may resize an image for a particular target device, but not for other target devices. In an embodiment, a developer may resize an image for all devices having a certain trait (e.g. 21" display).

In operation 720, the developer can enter and store other layer parameters and parameter values. Example layer parameters parameter values are described above with reference to FIG. 4, above.

In operation 725, the developer can optionally specify parameters for each layer for a specific target device. In embodiment, the developer can optionally specify parameters for each layer for a specific target device type. In an embodiment, the developer need not specify any target device type or device at all. Parameters may include resolution and size of an image, font and font size of text, or audio or video resolution, so as to optimize the balance of presentation quality and storage size for the image, font, audio, or video.

In operation 730, it is determined whether there are more layers to add to the layer stack image. If there are more layers to add to the layer stack image, then the method resumes at operation 710. If there are no more layers to add to the layer stack image, then in operation 735, the layer stack image can be stored for later compile and build of the application.

Figure 8:
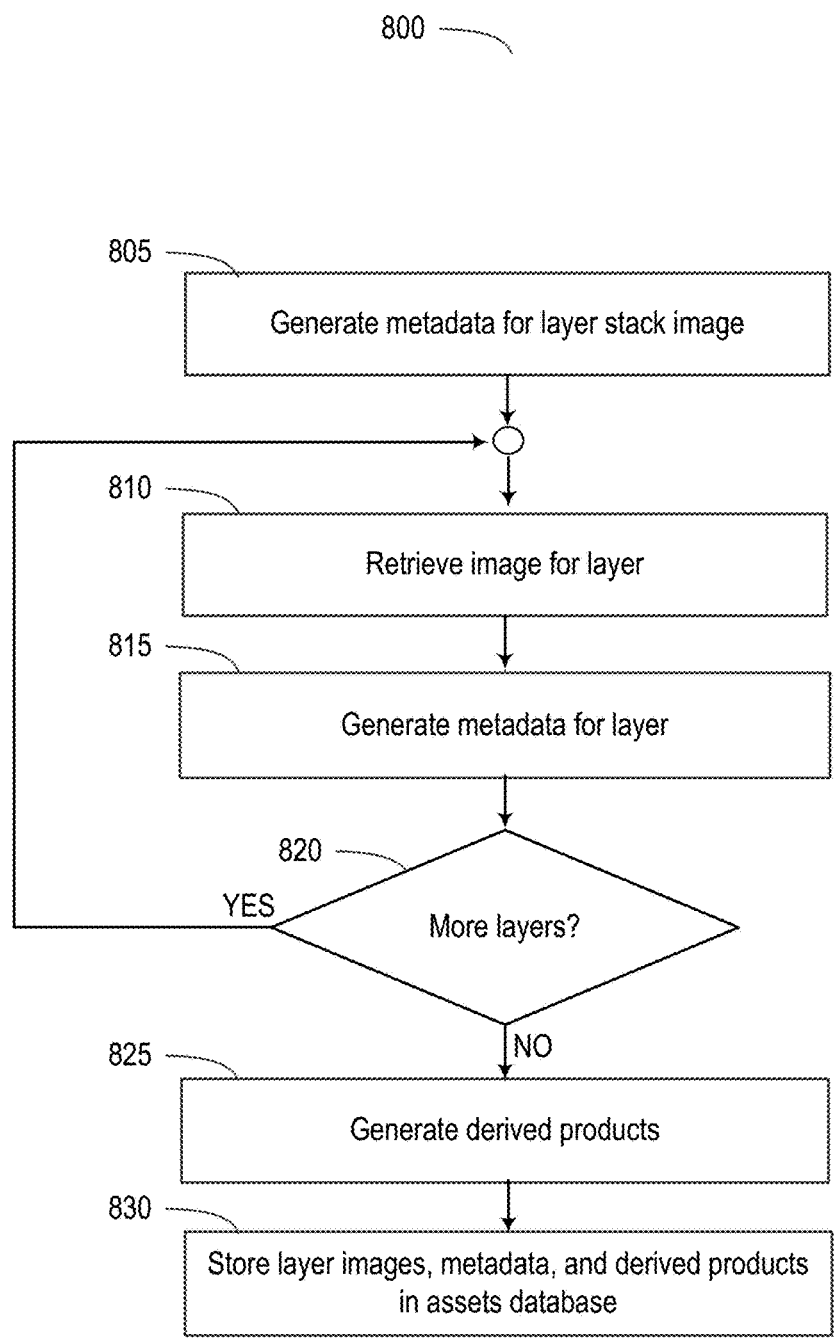
FIG. 8 illustrates, in block diagram form, a method of compiling and building an application that uses layer stack images.

FIG. 8 illustrates, in block diagram form, a method 800 of compiling and building an application that uses layer stack images.

In operation 805, a compile and build operation (collectively and individually, "compile") can generate metadata for each layer of a layer stack image. Metadata can describe one or more parameters and parameter values of the layer stack image, such as filename or textual description, and any target devices for the layer stack image, as exemplified with reference to FIG. 4, above.

In operation 810, an image for a layer of the layer stack image can be retrieved. The image can be locally stored, and retrieved from local storage. In an embodiment, a current copy of an image that is remotely referenced can be retrieved from the remote location and stored included in the asset catalog database that will store the compiled layer image stack.

In operation 815, metadata for the layer can be generated using the layer parameters and parameter values, as exemplified in FIG. 4, above.

In operation 820, it can be determined whether there are more layers in the layer stack image to process. If there are more layers in the layer stack to process, then method 800 results at operation 810. Otherwise method 800 proceeds to operation 825.

In operation 825, the compiler can generated derived products for the layer stack image. Derived products can include generating a flattened 2D image of the layer stack image. Derived products can also included generating a blurred image that represents an intermediate state, between motions, in an animated 3D effect that will be presented to the user when the application calls for the layer stack image. Derived products can also include modified versions of the image of the layer stack for different target devices, and different audio or video resolutions or formats for different target devices.

In operation 830, the compiler can store the layer image, variants of the layer image for different target devices, metadata describing the layer stack image and the individual layers of the layer stack image, and the derived products in an asset catalog database.

Figure 9:
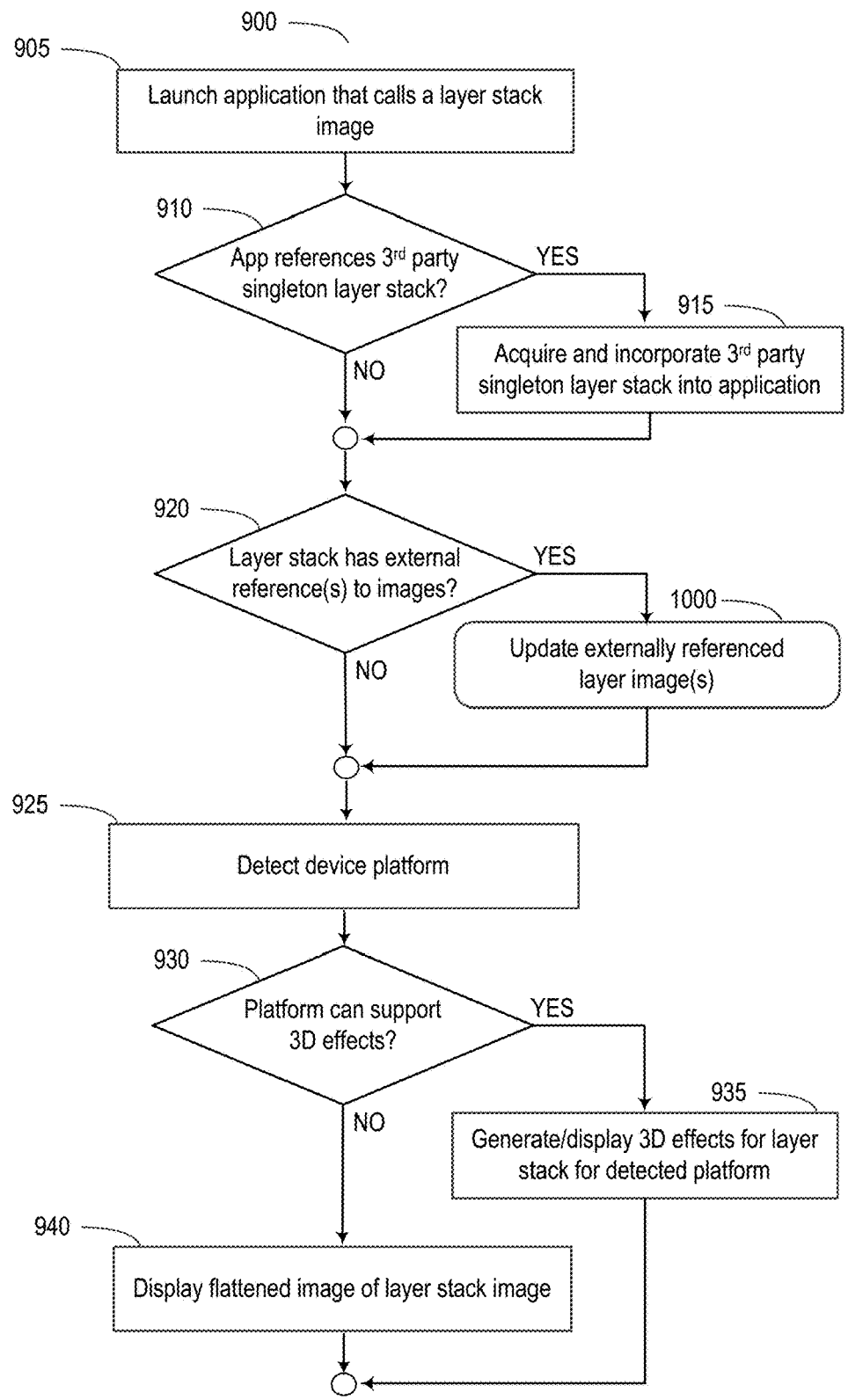
FIG. 9 illustrates, in block diagram form, a method of an application using layer stack images.

FIG. 9 illustrates, in block diagram form, a method 900 of an application using layer stack images.

In operation 905, an application that uses a layer stack image is launched.

In operation 910, it can be determined whether the application contains any references to third party layer stack images. Third party layer stack images can be authored and compiled as a single layer stack image (also termed "singleton" layer stack images). In an embodiment, the singleton can be compiled and stored in an asset catalog database containing only the single layer stack image. The singleton can be delivered to the application on request by the application.

If, in operation 910, it is determined that the application references a third party singleton layer stack image, then in operation 915, the application can request and receive the singleton layer stack image and incorporate the singled layer stack image into the application. In an embodiment, one or more singleton layer stack images can be received from a third party content provider and displayed in placeholder layer stack image template on a display screen. In an embodiment, one or more singleton layer stack images can be received by the application, extracted from the singleton asset catalog database, and stored in the application asset catalog database for later retrieval and display by the application. The method continues at operation 920.

If, in operation 910, it is determined that the application does not reference any third party singleton layer stack images, then method 900 continues at operation 920.

In operation 920, it can be determined whether the application references one or more layer stack images that contain an external reference to an image. For example, a layer stack image may contain a layer that contains a reference to an image of a third party logo that is stored somewhere other than in the assets catalog database of the application.

If, in operation 920, it is determined that one or more layer stack images contains an external reference to an image, then in operation 1000, the externally referenced image(s)

can be updated. Operation 1000 is described in detail with reference to FIG. 10, below. Method 900 continues at operation 925.

In operation 925, the application can detect the specific device that the application is running on.

In operation 930, it can be determined whether the specific device can support 3D effects of the layer stack images stored in the asset catalog database for the application.

If, in operation 930 it is determined that the specific device can display 3D effects for the layer stack images stored in the asset database for the application, then in operation 935, the application can generate the 3D effects for the application. In an embodiment, if the application calls for a layer stack image to display a 3D effect before the application has completed rendering the 3D effect for display, the application can display a flattened image of the layer stack image. When rendering of the 3D effect of the layer stack image is completed, then the application can display the 3D effect of the layer stack image.

If, in operation 930, it is determined that the specific device platform cannot support 3D images or effects of the layer stack images, then in operation 940 the application can display a flattened image for each layer stack image whose 3D image or effect cannot be displayed.

Figure 10:
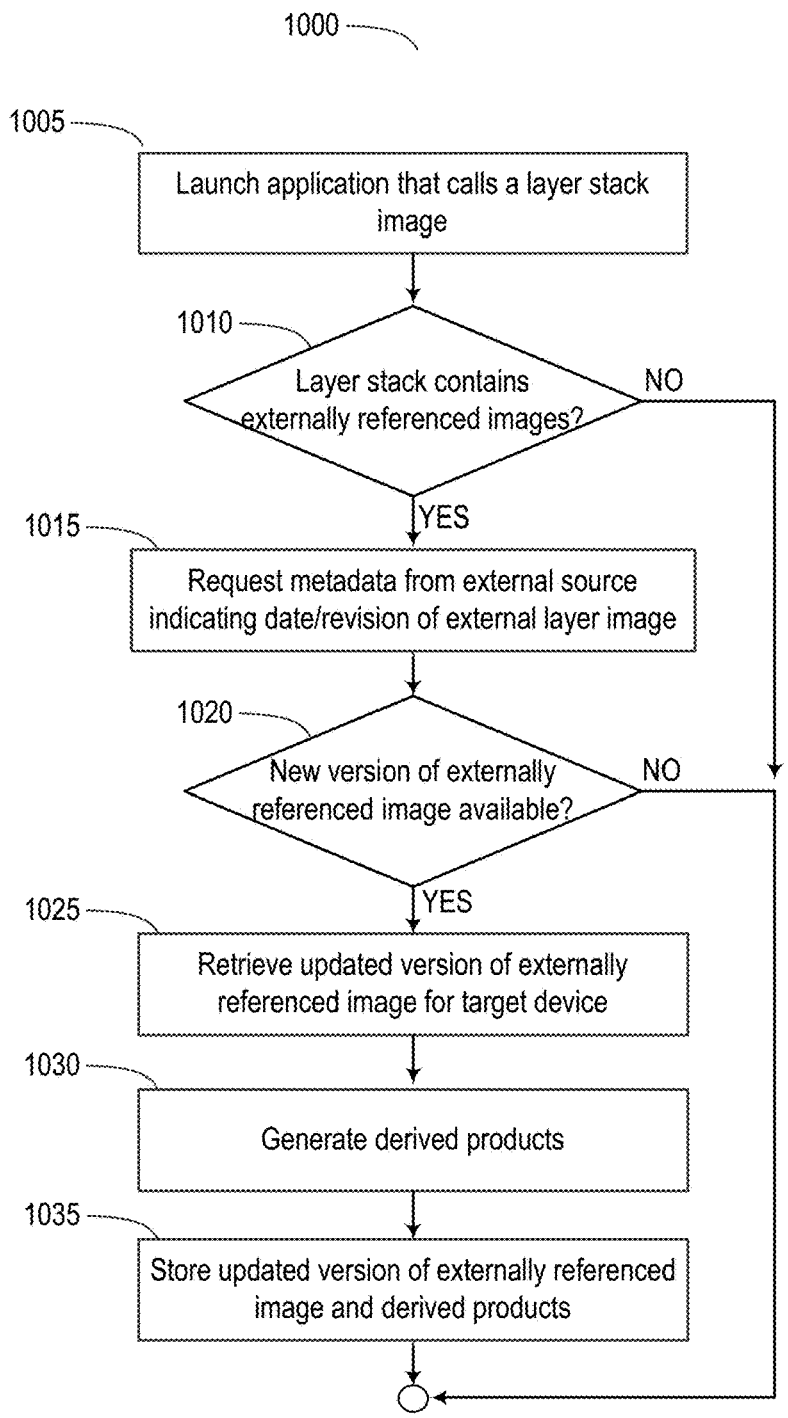
FIG. 10 illustrates, in block diagram form, a method of updating externally referenced images of a layer stack image.

FIG. 10 illustrates, in block diagram form, a method 1000 of updating externally referenced images of a layer stack image.

In operation 1005, an application that references one or more layer stack images can be launched.

In operation 1010, it can be determined whether any of the layer stack images referenced in the application contain an external reference to an image that is stored somewhere other than in the assets catalog database for the application.

If, in operation 1010, it is determined that the application references one or more layer stack images that contain an external reference to an image, then in operation 1015, for each externally referenced image, the application can download metadata from the external source where the externally referenced image can be obtained.

In operation 1020, the application can then compare the downloaded metadata with its own metadata in the assets catalog database and determine whether the externally referenced image has changed.

If, in operation 1020, it was determined that the externally referenced image has changed, then in operation 1025, the application can retrieve the updated version of the externally referenced image for the target device the application is running on. The application can stored the updated image and associated metadata in the asset catalog database.

In operation 1030, after an updated externally referenced image has been received, the application can generate updated derived products. Updated derived products can include a flattened image of the layer stack image and a blurred image of the layer stack image, both generated using the updated externally referenced image.

In operation 1035, the application can store the updated image, updated metadata for the updated image, and updated derived products in the assets catalog database for the application.

Figure 11:
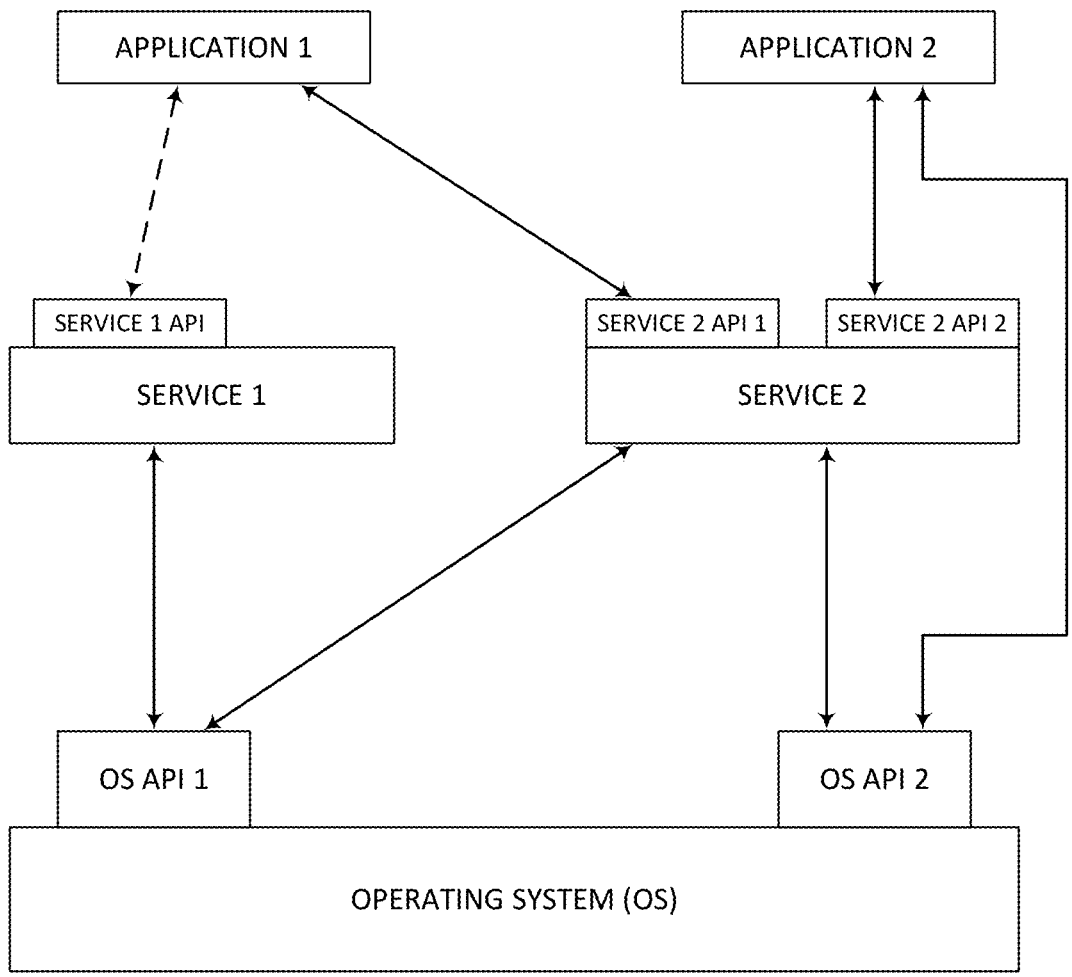
FIG. 11 illustrates an exemplary application programming interface (API) according to some embodiments.

In FIG. 11 ("Software Stack"), an exemplary embodiment, applications can make calls to Services 1 or 2 using several Service APIs and to Operating System (OS) using several OS APIs. Services 1 and 2 can make calls to OS using several OS APIs.

Note that the Service 2 has two APIs, one of which (Service 2 API 1) receives calls from and returns values to Application 1 and the other (Service 2 API 2) receives calls from and returns values to Application 2, Service 1 (which can be, for example, a software library) makes calls to and receives returned values from OS API 1, and Service 2 (which can be, for example, a software library) makes calls to and receives returned values from both OS API 1 and OS API 2, Application 2 makes calls to and receives returned values from OS API 2.

Figure 12:
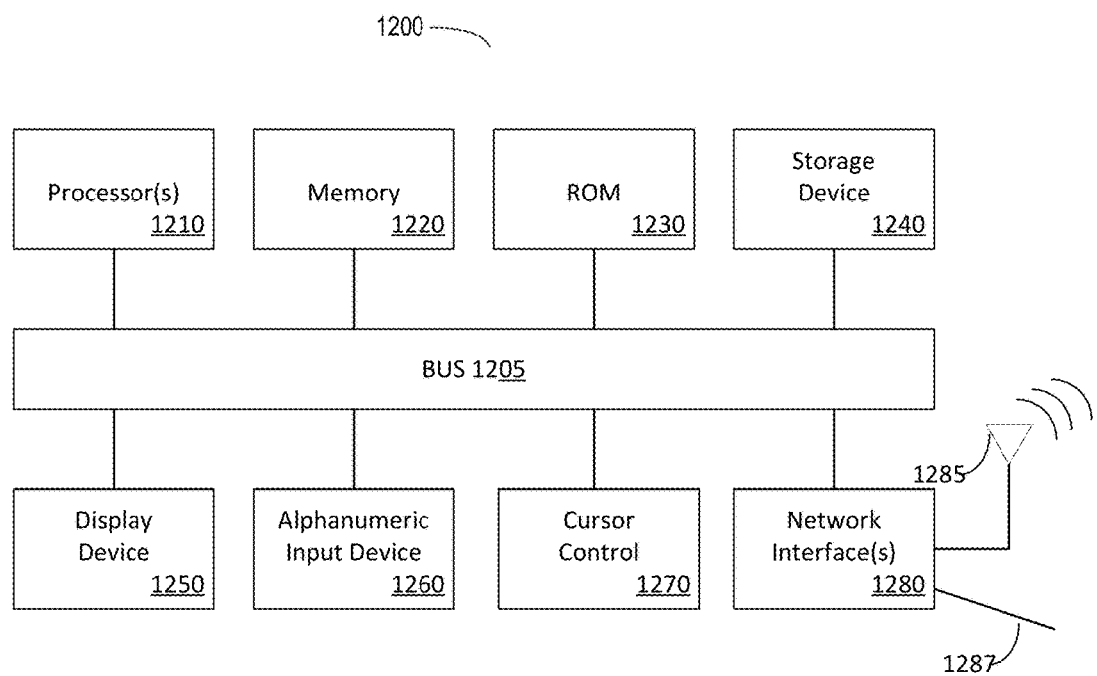
FIG. 12 is a block diagram of one embodiment of a computing system.

FIG. 12 is a block diagram of one embodiment of a computing system 1200. The computing system illustrated in FIG. 12 is intended to represent a range of computing systems (either wired or wireless) including, for example, desktop computer systems, laptop computer systems, cellular telephones, personal digital assistants (PDAs) including cellular-enabled PDAs, set top boxes, entertainment systems or other consumer electronic devices. Alternative computing systems may include more, fewer and/or different components. The computing system of FIG. 12 may be used to provide the computing device and/or the server device.

Computing system 1200 includes bus 1205 or other communication device to communicate information, and processor 1210 coupled to bus 1205 that may process information.

While computing system 1200 is illustrated with a single processor, computing system 1200 may include multiple processors and/or co-processors 1210. Computing system 1200 further may include random access memory (RAM) or other dynamic storage device 1220 (referred to as main memory), coupled to bus 1205 and may store information and instructions that may be executed by processor(s) 1210. Main memory 1220 may also be used to store temporary variables or other intermediate information during execution of instructions by processor 1210.

Computing system 1200 may also include read only memory (ROM) and/or other static storage device 1240 coupled to bus 1205 that may store static information and instructions for processor(s) 1210. Data storage device 1240 may be coupled to bus 1205 to store information and instructions. Data storage device 1240 such as flash memory or a magnetic disk or optical disc and corresponding drive may be coupled to computing system 1200.

Computing system 1200 may also be coupled via bus 1205 to display device 1250, such as a cathode ray tube (CRT) or liquid crystal display (LCD), to display information to a user. Computing system 1200 can also include an alphanumeric input device 1260, including alphanumeric and other keys, which may be coupled to bus 1205 to communicate information and command selections to processor(s) 1210. Another type of user input device is cursor control 1270, such as a touchpad, a mouse, a trackball, or cursor direction keys to communicate direction information and command selections to processor(s) 1210 and to control cursor movement on display 1250.

Computing system 1200 further may include one or more network interface(s) 1280 to provide access to a network, such as a local area network. Network interface(s) 1280 may include, for example, a wireless network interface having antenna 1285, which may represent one or more antenna(e). Computing system 1200 can include multiple wireless network interfaces such as a combination of WiFi, Bluetooth® and cellular telephony interfaces. Network interface(s) 1280 may also include, for example, a wired network interface to communicate with remote devices via network cable 1287, which may be, for example, an Ethernet cable, a coaxial cable, a fiber optic cable, a serial cable, or a parallel cable.

In one embodiment, network interface(s) 1280 may provide access to a local area network, for example, by conforming to IEEE 802.11b and/or IEEE 802.11g standards, and/or the wireless network interface may provide access to a personal area network, for example, by conforming to Bluetooth standards. Other wireless network interfaces and/or protocols can also be supported. In addition to, or instead of, communication via wireless LAN standards, network interface(s) 1280 may provide wireless communications using, for example, Time Division, Multiple Access (TDMA) protocols, Global System for Mobile Communications (GSM) protocols, Code Division, Multiple Access (CDMA) protocols, and/or any other type of wireless communications protocol.

In the foregoing specification, the invention has been described with reference to specific embodiments thereof. It will, however, be evident that various modifications and changes can be made thereto without departing from the broader spirit and scope of the invention. The specification and drawings are, accordingly, to be regarded in an illustrative rather than a restrictive sense.

What is claimed is:

1. A computer-implemented method, comprising:
    authoring a layer stack image to be displayed during run-time of an application, wherein the layer stack image is displayable on a plurality of different target device types, without specifying a particular target device type during the authoring, wherein authoring the layer stack image comprises:
        specifying a plurality of images that will be used to author the layer stack image, wherein the layer stack image comprises a three-dimensional (3D) image;
        generating a modified version of at least one image of the plurality of images for use with a particular target device type;
        for each image of the plurality of images, specifying a plurality of parameters and corresponding parameter values of the image;
    compiling the layer stack image to generate a three-dimensional (3D) image and a two-dimensional (2D) flattened image from the layer stack image, wherein compiling the layer stack image comprises:
        generating metadata that describes the layer stack image;
        for each image of the plurality of images, generating metadata that describes the plurality of parameters and corresponding parameter values for the layer and image;
        generating executable code that, when executed on a target device having a target device type in the plurality of different target device types, displays the layer stack image on the target device during run-time of the application;
    storing the metadata that describes the layer stack image, the generated executable code, and, for each image, storing at least a reference to the image or a copy of the image.

2. The method of claim 1, wherein specifying an image in the plurality of images comprises specifying a reference to an image that is stored at a remote location.

3. The method of claim 1, further comprising:
    specifying a layer of the layer stack image that comprises text, and wherein one or more of the plurality of parameters and corresponding values comprise the text of the layer and one or more font characteristics of the text.

4. The method of claim 1, wherein one or more of the plurality of parameters and corresponding parameter values of a layer in the plurality of layers includes a reference to one of an audio clip, a video clip, an audio/video clip, or an animation.

5. The method of claim 1, further comprising:
    specifying a plurality of target devices upon which the layer stack image is intended to be displayed, wherein specifying a target device includes at least one of: specifying a type of the target device or specifying a manufacturer and model of the target device, wherein a type of the target device includes a desktop computer, a laptop computer, a tablet computer, a smart phone, or a media presentation device.

6. The method of claim 1, wherein
    an opacity of at least one image in the plurality of images is greater than zero.

7. The method of claim 1, wherein, for at least one layer of the layer stack image, storing both a reference to the image of the layer and a copy of the image for the layer.

8. The method of claim 1, wherein compiling the layer stack image comprises compiling only a single layer stack image.

9. The method of claim 1, wherein the metadata for the layer stack image, the metadata for each layer of the layer stack image, and the at least either a reference to an image for a layer or a copy of the image for the layer, are stored in an asset catalog database that can be accessed at run-time by an application that requests the layer stack image.

10. The method of claim 1, wherein generating a modified version of at least one of the plurality of images for use with a particular target device comprises:
    modifying a video resolution associated with an image in the plurality of images, modifying an audio resolution of audio associated with an image in the plurality of images, resizing an image, or modifying a format of an image in the plurality of images.

11. The method of claim 1, wherein compiling the layer stack image further comprises:
    detecting that a target device in the plurality of target devices does not support 3D rendering and effects;
    wherein the 2D flattened image is obtained by thinning one or more layers from the 3D layer stack image, leaving the 2D flattened image remaining for display on the target device that does not support 3D rendering and effects.

12. The method of claim 1, wherein the storing is to an asset catalog that contains a version of the layer stack image that is displayable on each of the plurality of different target devices types.

13. A non-transitory computer readable medium programmed with instructions that, when executed by a processing system, perform a method, comprising:
    authoring a layer stack image to be displayed during run-time of an application, wherein the layer stack image is displayable on a plurality of different target device types, without specifying a particular target device type during the authoring, wherein authoring the layer stack image comprises:
        specifying a plurality of images that will be used to author the layer stack image, wherein the layer stack image comprises a three-dimensional (3D) image;
        generating a modified version of at least one image of the plurality of images for use with a particular target device type;
        for each image of the plurality of images, specifying a plurality of parameters and corresponding parameter values of the image;

compiling the layer stack image to generate a three-dimensional (3D) image and a two-dimensional (2D) flattened image from the layer stack image, wherein compiling the layer stack image comprises:
  generating metadata that describes the layer stack image;
  for each image of the plurality of images, generating metadata that describes the plurality of parameters and corresponding parameter values for the layer and image;
  generating executable code that, when executed on a target device having a target device type in the plurality of different target device types, displays the layer stack image on the target device during run-time of the application;
  storing the metadata that describes the layer stack image, the generated executable code, and, for each image, storing at least a reference to the image or a copy of the image.

14. The medium of claim 13, wherein specifying an image in the plurality of images comprises specifying a reference to an image that is stored at a remote location.

15. The medium of claim 13, further comprising:
specifying a layer of the layer stack image that comprises text, and wherein one or more of the plurality of parameters and corresponding values comprise the text of the layer and one or more font characteristics of the text.

16. The medium of claim 13, wherein one or more of the plurality of parameters and corresponding parameter values includes a reference to one of an audio clip, a video clip, an audio/video clip, or an animation.

17. The medium of claim 13, further comprising:
specifying a plurality of target devices upon which the layer stack image is intended to be displayed, wherein specifying a target device includes at least one of: specifying a type of the target device or specifying a manufacturer and model of the target device, wherein a type of the target device includes a desktop computer, a laptop computer, a tablet computer, a smart phone, or a media presentation device.

18. The medium of claim 13, wherein
an opacity of at least one image in the plurality of images is greater than zero.

19. The medium of claim 13, wherein, for at least one layer of the layer stack image, storing both a reference to the image of the layer and a copy of the image for the layer.

20. The medium of claim 13, wherein compiling the layer stack image comprises compiling only a single layer stack image.

21. The medium of claim 13, wherein the metadata for the layer stack image, the metadata for each layer of the layer stack image, and the at least either a reference to an image for a layer or a copy of the image for the layer, are stored in an asset catalog database that can be accessed at run-time by an application that requests the layer stack image.

22. A system comprising:
a processing system coupled to a memory programmed with executable instructions that, when executed by the processing system perform a method, comprising:
authoring a layer stack image to be displayed during run-time of an application, wherein the layer stack image is displayable on a plurality of different target device types, without specifying a particular target device type during the authoring, wherein authoring the layer stack image comprises:
  specifying a plurality of images that will be used to author the layer stack image, wherein the layer stack image comprises a three-dimensional (3D) image;
  generating a modified version of at least one image of the plurality of images for use with a particular target device type;
  for each image of the plurality of images, specifying a plurality of parameters and corresponding parameter values of the image;
  compiling the layer stack image to generate a three-dimensional (3D) image and a two-dimensional (2D) flattened image from the layer stack image, wherein compiling the layer stack image comprises:
    generating metadata that describes the layer stack image;
    for each image of the plurality of images, generating metadata that describes the plurality of parameters and corresponding parameter values for the layer and image;
    generating executable code that, when executed on a target device having a target device type in the plurality of different target device types, displays the layer stack image on the target device during run-time of the application;
    storing the metadata that describes the layer stack image, the generated executable code, and, for each image, storing at least a reference to the image or a copy of the image.

23. The system of claim 22, wherein specifying an image in the plurality of images comprises specifying a reference to an image that is stored at a remote location.

24. The system of claim 22, further comprising:
specifying a layer of the layer stack image that comprises text, and wherein one or more of the plurality of parameters and corresponding values comprise the text of the layer and one or more font characteristics of the text.

25. The system of claim 22, wherein one or more of the plurality of parameters and corresponding parameter values includes a reference to one of an audio clip, a video clip, an audio/video clip, or an animation.

26. The system of claim 22, further comprising:
specifying a plurality of target devices upon which the layer stack image is intended to be displayed, wherein specifying a target device includes at least one of: specifying a type of the target device or specifying a manufacturer and model of the target device, wherein a type of the target device includes a desktop computer, a laptop computer, a tablet computer, a smart phone, or a media presentation device.

27. The system of claim 22, wherein
an opacity of at least one image in the plurality of images is greater than zero.

28. The system of claim 22, wherein, for at least one layer of the layer stack image, storing both a reference to the image of the layer and a copy of the image for the layer.

29. The system of claim 22, wherein compiling the layer stack image comprises compiling only a single layer stack image.

30. The system of claim 22, wherein the metadata for the layer stack image, the metadata for each layer of the layer stack image, and the at least either a reference to an image for a layer or a copy of the image for the layer, are stored in an asset catalog database that can be accessed at run-time by an application that requests the layer stack image.

* * * * *